United States Patent [19]

Lau et al.

[11] Patent Number: 4,708,020
[45] Date of Patent: Nov. 24, 1987

[54] TEMPERATURE COMPENSATING CONTINUOUS PANEL TESTER

[75] Inventors: Kenneth K. Lau, Vancouver; Jack T. Yelf, West Vancouver, both of Canada

[73] Assignee: MacMillan Bloedel Limited, Vancouver, Canada

[21] Appl. No.: 3,839

[22] Filed: Jan. 16, 1987

Related U.S. Application Data

[63] Continuation-in-part of Ser. No. 849,189, Apr. 7, 1986, abandoned.

[51] Int. Cl.[4] .............................. G01N 3/20
[52] U.S. Cl. ....................... 73/852; 374/142
[58] Field of Search ............... 73/852, 854, 849, 853, 73/812; 374/52, 120, 121, 142

[56] References Cited

U.S. PATENT DOCUMENTS

| | | | |
|---|---|---|---|
| 3,143,878 | 8/1964 | Hoyle, Jr. et al. | 73/852 |
| 3,194,063 | 7/1965 | McKean | 73/852 |
| 3,196,672 | 7/1965 | Keller | 73/812 |
| 4,313,348 | 2/1982 | Madsen | 73/852 |
| 4,408,903 | 10/1983 | Baldasarri | 374/121 |

FOREIGN PATENT DOCUMENTS

| | | | |
|---|---|---|---|
| 1015222 | 12/1965 | United Kingdom | 73/852 |
| 1322953 | 7/1973 | United Kingdom | 73/849 |

OTHER PUBLICATIONS

Metriguard, Inc. brochure, "Portable Stress Wave Timer", 1980.
Metriguard, Inc. brochure, "In-Line Stress Wave System", 1978.

*Primary Examiner*—Stewart J. Levy
*Assistant Examiner*—Robert R. Raevis
*Attorney, Agent, or Firm*—C. A. Rowley

[57] ABSTRACT

An apparatus and process for testing a panel for strength and stiffness has the ability to handle panels of different thicknesses, and also has a temperature sensor so that panels can be tested hot and the cold end use strength and stiffness correlated. The apparatus moves the panel in an "S" shaped path through a series of rollers, and measures the load to deflect the panel a predetermined distance for different thicknesses of panels. An algorithm is used to correlate the cold end use strength and stiffness values from the temperature and loading figures.

17 Claims, 8 Drawing Figures

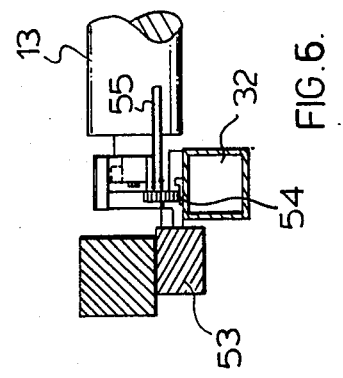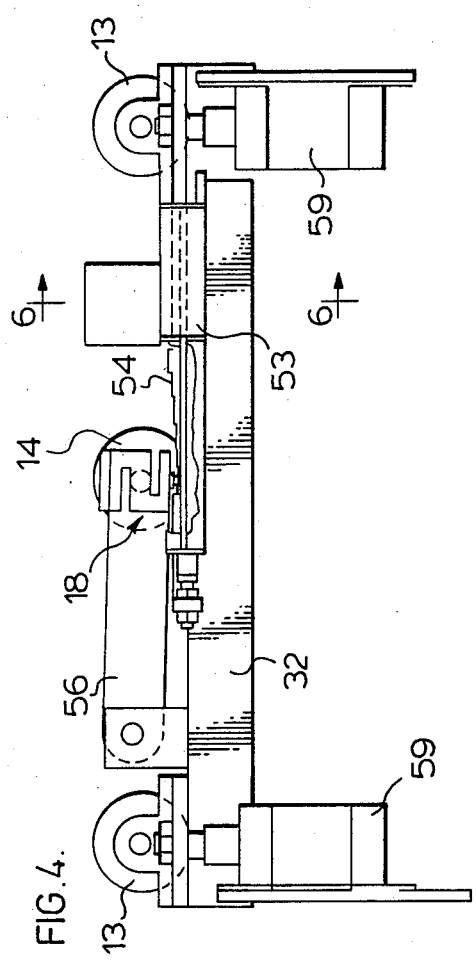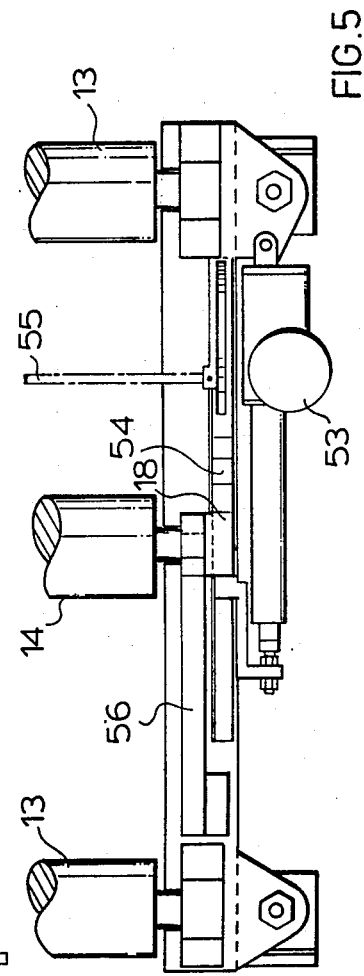

TEMPERATURE COMPENSATING CONTINUOUS PANEL TESTER

This application is a Continuation In Part of application Ser. No. 849,189 filed Apr. 7, 1986 now abandoned.

The present invention relates to nondestructive testing of composite panels to determine both strength and stiffness. More specifically, the present invention provides an apparatus and a process for determining strength and stiffness of composite panels having different thicknesses and/or correlating end use strength and stiffness when the testing is carried out on hot panels.

In the production of composite wood panels such as waferboard, plywood, strand board and any other type of composite panels that are prepared in a press with a resin binder, it is necessary to know the stiffness and strength of the end product. In the past, samples of products were taken off a panel line and tested. The testing was generally carried out on individual sample panels after they were cool and a Modulus of Elasticity (MOE) calculated for these panels. Because there is a time delay between production and testing, this procedure does not lend itself to an efficient feed back control for the process.

There are three potential methods of testing for stiffness. One is the resonant frequency method whereby a panel is vibrated and its resonant frequency measured. This method does not perform well for low stiffness panels as the panels tend to sag and proper vibration cannot be obtained. A second method is the stress wave method where a sonic wave is transmitted across a face of a panel and the time for the sonic wave to travel across the panel measured. This time value is used to determine stiffness. The method does not identify delaminations or low density defects in the panel. The third accepted method of testing for stiffness is referred to as the bending method wherein a panel is deflected as it passes through an "S" shaped path. Either the deflection may be measured for a specific load or the load is measured for a particular deflection. In practice it has been found simpler to force a panel to produce a constant deflection and measure the load for that deflection. In this method, the panel always follows a predetermined S-shaped path.

One example of such a testing device is disclosed in U.S. Pat. No. 3,196,672 to Keller. This device relates to measuring the stiffness of "dimension lumber". This machine, known in the trade as the "Continuous Lumber Tester", is not suitable for testing panels because it is designed to test only one thickness of material (i.e. 1½ inch thick lumber) whereas panels are manufactured in a range of thickness. Furthermore, the tester is limited to a lumber width which is too limited for panels, particularly panels as they come off a press. The tester is designed to calculate a stiffness of the lumber being tested, but cannot compensate stiffness due to temperature change.

The present invention provides a testing machine suitable for on-line testing for different thicknesses of panel products. The panels may be tested at one temperature, approaching the press temperature and the stiffness and strength determined for the end product at another temperature (generally ambient or end use temperature). Furthermore, the testing machine allows panels to be graded so rejects can be identified and panels can be separated into grade groups representing different stiffness and strength ranges.

The continuous panel tester of the present invention is a roll conveyor that imposes a double reverse bend or S-shaped configuration on a panel as it passes through the conveyor at line speed. The load required to form this S-shaped configuration is used to calculate the MOE based on nominal panel thickness. The severity of the S-shaped configuration is limited so that the stress applied to the panel does not damage it, particularly if the panel is still hot. The S-shaped configuration is changed by repositioning the rolls for each nominal thickness of the panel.

In one embodiment pneumatic cylinders move the rollers into preset positions which in turn are prepositioned by electro mechanical actuators. A suitable nip pressure is applied to the panel and several of the rolls are powered to drive the panel through the conveyor.

In another embodiment, a marker can be used to mark the grade of stiffness on the panel.

In a still further embodiment, an algorithm is used to correlate stress values determined on hot panels to end use values.

The present invention provides an apparatus and a process that enables an end use MOE of a composite wood panel with a thermosetting resin binder to be determined even though the panel is tested while it is still hot. Furthermore, the apparatus may be positioned using a micro-processor to test different thicknesses of panel by merely selecting the required nominal panel thickness. The micro-processor is programmed to control the equipment to position the rolls of the machine to process panels of the selected nominal thickness.

In one embodiment, the micro-processer is linked to a marking device so the particular grade of panel can be determined by the tester and then marked directly onto the panel itself. The panel rejects may be discarded and the acceptable panels directed to appropriate grade bins.

The present invention provides an apparatus for determining stiffness and strength of a composite panel moving in a path after exiting from a press, comprising: plurality of rolls positioned to guide the panel in an "S" shaped path, deflector means to deflect the panel from top and bottom for a predetermined deflection as the panel moves in the "S" shaped path, load measuring means to measure load to deflect the panel from the top and from the bottom, temperature sensing means to measure the temperature of the panel being tested, calculation means to determine stiffness and strength of the hot panel from the deflection load, correlation means to determine cold end use stiffness and strength of the panel from the temperature of the panel being tested. In a preferred embodiment, the correlation means comprises a micro-processor utilizing the program that determines the stiffness and strength figures for the panel at ambient or end use temperatures.

In another embodiment of the present invention, an apparatus is provided for determining stiffness and strength of different thicknesses of composite panels moving in a path, comprising plurality of rolls positioned to guide a panel in an "S" shaped path, deflector means to deflect the panel from top and bottom for a predetermined deflection as the panel moves in the "S" shaped path, load measuring means to measure load to deflect the panel from the top and from the bottom, calculation means to determine the stiffness and strength of the panel from deflection and deflection load, and adjustment means to vary position of the rolls and predetermined deflection of the panel from the top and from the bottom for different thicknesses of the panel. In one embodiment the adjustment means to vary position of the rolls and the predetermined deflection of the panel is actuated from a single control selecting thickness of the panel to be tested.

In yet another embodiment, the present invention provides an on-line method to determine stiffness and strength of a composite panel after exiting from a press and still hot, comprising the steps of feeding the panel in an "S" shaped path between a plurality of pairs of rolls, deflecting the panel from both sides and measuring the deflection load from a predetermined deflection, measuring the temperature of the panel being tested, calculating hot stiffness and strength of the panel from the deflection load, and correlating cold end use stiffness and strength of the panel from the temperature of the panel being tested.

In another embodiment, the correlating step is performed by utilizing an algorithm developed for cold end use stiffness and strength properties for a panel versus panel temperatures.

In drawings which illustrate embodiments of the invention:

FIG. 4 shows a side elevation of one deflector roll and loading frame for the tester shown in FIG. 2;

FIG. 5 shows a partial plan view of the deflector roll shown in FIG. 4;

FIG. 6 shows a cross-section taken at line 6—6 of FIG. 4;

When composite panels, such as waferboard panels, emerge from a press, they have a surface temperature that can be as high as 220 degrees Celcius. Thus if the panel is tested at this temperature, the figures produced represent hot stiffness and strength properties. These figures must be correlated to show the properties of the panel at ambient temperature.

Figure 1:
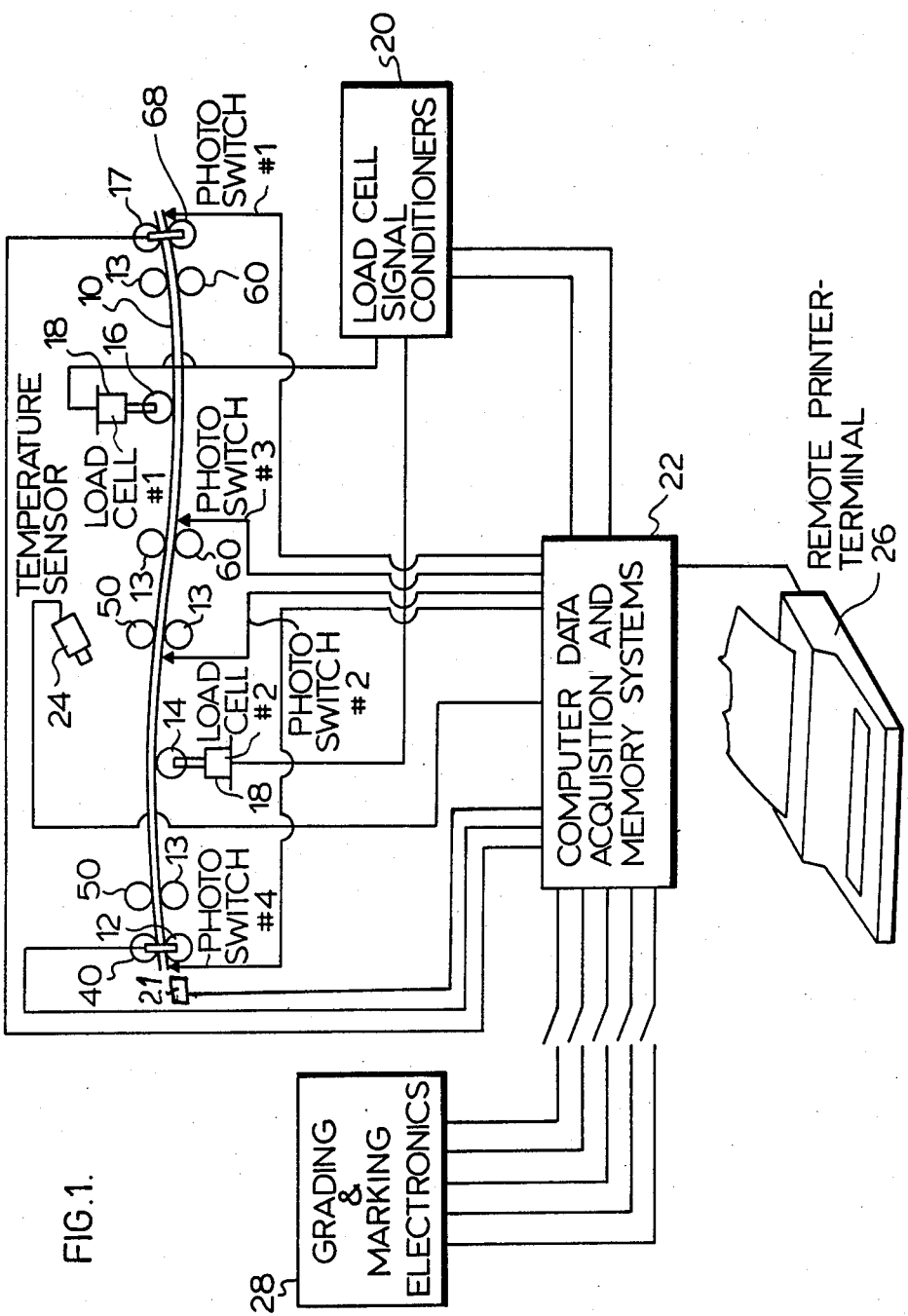
FIG. 1 shows a schematic block diagram of an on-line panel tester according to one embodiment of the present invention.

FIG. 1 illustrates an on-line testing apparatus wherein a composite panel 10 moves in an "S" shaped path. A pair of cooperating in-feed guide rolls 12 and 40 guide the panel 10 past the first pair of spaced positioning rolls 13 each of which cooperates with its respective reaction roll 50 to clamp the panel 10 therebetween and position the panel 10 against the reaction rolls 50. The first deflector roll 14 is positioned midway between the rolls 13 and functions to bend the panel in a first direction into the first curved portion of the "S" shaped path.

The panel then passes and is guided by a second pair of spaced positioning rolls 13 each of which cooperates with its respective reaction roll 60 to clamp the panel 10 there between. The second deflection roll 16 is positioned substantially midway between the second pair of positioning rolls 13 and bends the panel in a second direction opposite to the first direction in which the panel is bent by roll 14 and into the second curved portion of the "S" shaped path, i.e. in a reverse curvature to that formed by the first deflection roll 14. The panel 10 then exits through a pair of cooperating out-feed guide rolls 17 and 68. The arrangements of the guide rolls 12 and 40, 17 and 68, positioning rolls 13, reaction rolls 50 and 60 and deflector rolls 14 and 16 will be described in more detail hereafter. The deflector rolls 14 and 16 each have a load cell 18 which feeds a signal to a load cell signal conditioner 20 which in turn feeds a signal to a micro-processor 22. The positions of the guide rolls 12, 17, 40 and 68, positioning rolls 13, reaction rolls 50 and 60 and deflector rolls 14 and 16 may all be controlled by the micro-processor 22. A temperature sensor 24, which is preferably an infra-red sensor, senses the temperature of the panel 10 being tested and this information is fed to the microprocessor 22. The microprocessor 22 utilizes the information from the load cells 18 to calculate hot stiffness and strength properties for the selected nominal thickness, then correlates these figures with the temperature and by use of a preprogrammed algorithm determines the ambient or cold end use strength and stiffness properties for the panel. This information is shown on a printed terminal 26. Furthermore, the microprocessor 22 can grade each panel within predetermined grades of stiffness and strength by utilizing the grading and marketing electronics 28.

For grading purposes the use of nominal thickness if preferred by if more accurate calculation of strength and stiffness properties is desired a suitable thickness sensor 21 such as well known thickness sensors operating, for example, on the basis of laser sensing or ultrasonic sensing that are capable of providing a thickness measurement as the panels are fed through the machine may be used and the actual instead of the nominal thickness used in determining the strength and stiffness of the panel. The on-line thickness measurement obviously could also be used in monitoring plant operation.

The information from the microprocessor 22 can be used as a feed back control. This is particularly suitable when the tester is positioned on-line so that every panel is tested shortly after leaving the press.

The panels may be graded, identifying rejects which are discarded and the end use stiffness and strength figures marked on each panel, which has not previously been possible on an in-line machine. Furthermore, the panels may be sorted out into different grade bins, allowing the higher grade panels to be sold at a preium price.

The tester can be used for substantially all panel products. Typically, panels of widths up to approximately 8 feet and thicknesses of from ⅛ inch up to 1½ inches may be used. These parameters are particularly suitable to waferboard and plywood panels.

Photo switches 1, 2, 3 and 4 are used to determine that a panel is in the tester. The switches are used to ensure that readings from the load cell and temperature sensor represent strength and stiffness figures for one panel. The photo switches determine when one panel ends, and a second panel commences to pass through the tester. There is preferably a gap of at least 1 inch between panels. Panels pass through the tester at line speeds up to at about 300 feet/min. Readings from the load cells and temperature sensors are taken at predetermined intervals, for example, every 20 milliseconds. The microprocessor averages the stiffness and strength figures for each panel.

Figure 2:
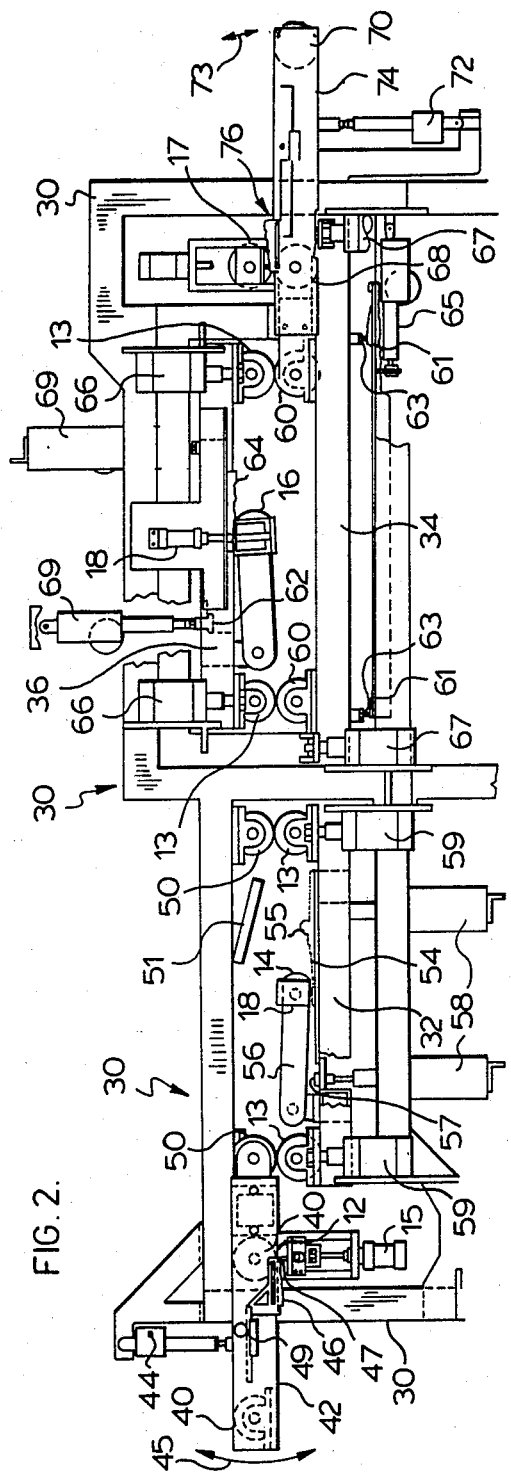
FIG. 2 shows a side elevation of a continuous panel tester with parts omitted for clarity and illustrating one embodiment of the present invention.

As can be seen in FIG. 2, the machine is composed of a main frame 30 which has three sub-frames therein, a first loading frame 32 which supports the first deflector roll 14 and two lower positioning rolls 13; a second articulated sub-main frame 34 which supports the second half of the machine and includes a second loading frame 36 supporting the second deflector roll 16 and two upper positioning rolls 13. The second articulated submain frame 34 also supports the out-feed guide rolls 17, 68, etc.

Figure 3:
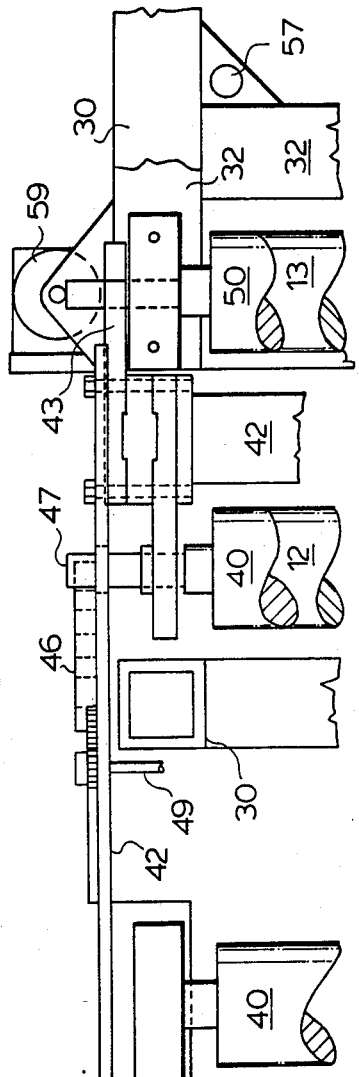
FIG. 3 shows an enlarged (relative to FIG. 1) partial plan view of the entry rolls for the tester shown in FIG. 2.

Two top in-feed rolls 40 are supported on an in-feed arm 42 which is pivotably mounted on the axis of rotation of the adjacent reaction roll 50 on arm extensions 43 (only one shown, see FIG. 3). The angular position of arm 42 is adjusted by a screw type actuator 44 which pivots the arm 42 around the axis of roll 50 as indicated by arrow 45 in accordance with a predetermined position or a given amount of deformation or curvature of the panel as defined by the position of roll 14 relative to frame 32, i.e. the configuration of the "S" shaped path.

The top in-feed roll 40 closer to the adjacent roll 50 forms the top roll of an in-feed guide nip with the roll 12. The spacing between the roll 12 and its cooperating nip forming roll 40 is adjusted by a step cam 46 which separates the rolls 12 and 40 to the required degree depending on the thickness of the panel being tested. The position of the roll 12 is determined by the step cam 46 engaged by the abutment 47 on the mounting for roll 12. There are step cams at opposite ends of the roll 12 and they are moved in synchronism by the mechanism 49. The stops 47 are held against the cams 46 by pneumatic spring 15.

As above indicated the angle of the arm 42 is changed depending on the position of the roll 14 which in turn determines the degree of bending of the panel 10. The panel 10 passes over the pair of rolls 13 and is deformed by the roll 14 pressing the panel against the rolls 50 causing the panel to bend.

When the lead end of the panel passes over the roll 14 its direction of travel will not intersect with the nip formed between the next pair of rolls 13 and 50 in the sequence thus a deflector 51 is provided to deflect the leading end of the panel into the nip formed between the next pair of rolls 13 and 50 in the sequence.

Deflector roll 14 is mounted on the first loading frame 32 via an arm 56 pivoted on the frame 32 there being an arm 56 at each end of roll 14. The position of the roll 14 relative to the remainder of the frame 32 is determined by step cam 54 which is moved along the frame 32 by a screw type actuator 53 (see FIGS. 4, 5 and 6) as desired to impose a thicker or thinner step between the load cell 18 supporting the roll 14 and the frame 32, to cause the arm 56 to pivot on its axis and position the roll 14 at the desired spacing from the remainder of the frame 32. It is to be understood the roll 14 is symetrically supported at each end and the cams 54 at opposite ends of the roll 14 are interconnected by a mechanism 55 so the cams are moved in unison (see FIGS. 2, 5 and 6). The roll 14 is thus positioned a selected distance above the horizontal plane interconnecting the upper portions of the peripheries of the two spaced rolls 13 thereby to impose the desired degree of bending to the panel being tested.

Actuators 58 are provided (one for each corner of frame 32) to accurately adjust the positions of stops 57 (only one shown) that limit the vertical upward movement of the frame 32 and are set depending on the thickness of the panel to be tested to provide the desired gap between the rolls 13 and 50. Pneumatic cylinders 59 (one in each corner of frame 32) when no panel is in position force the frame 32 into position against the present stops 57 positioned by the actuators 58. Normally, the gap between each pair of cooperating rolls 50 and 13 will be slightly smaller than the thickness of the panel to be tested so that when a panel passes therebetween the pneumatic cylinders 59 absorb this difference in thickness while maintaining the rolls 13 in contact with the adjacent face of the panel 10 being tested.

Generally, when the panel thickness is changed the position of the roll 14 (as well as roll 16) is changed so that the degree of deformation of the panel changes and the "S" shaped path is thus varied.

The second articulated sub-main frame 34 is moved up or down depending upon the required "S" shaped configuration by any suitable positioning means. In the illustrated arrangement suitable step cams 61 are engaged by stops 63, there being a step cam 61 and stop 63 in each corner of the frame 34. The step cams 61 are interconnected and their positions all adjusted by actuator 65. Suitable means such as pneumatic cylinders 67 one at each corner of the frame 34 lift the frame 34 for adjustment of step cams 61 and hold the frame 34 down with the stops 63 against the step cams 61.

The second loading frame 36 is substantially the same as the first loading frame 32, but is inverted with the second deflector roll 16 pushing down on the panel between the two positioning rolls 13 which cooperate with reaction rolss 60. Step cams 64 (only one shown) are provided for positioning the second deflector roll 16 and pneumatic cylinders 66 move the frame 36 to the required position relative to frame 34 as determined by actuators 69 which position the stops 62 (only one shown). Step cams 64, cylinders 66, actuators 67 and stops 62 are similar to step cam 54, cylinders 59, actuators 58 and stops 57 and function in same manner to adjust the position of roll 16 relative to frame 36 and frame 36 relative to frame 34 as do the cams 54 in adjusting the position of roll 14 relative to frame 32 and the cylinders 59 and actuators 58 and stops 57 in adjusting frame 32 relative to frame 30. It will be apparent that because the roll 16 is beneath the frame 36 it will be mounted in a suitable manner to prevent it from falling out of position.

A deflector shoe (not shown but equivalent to shoe 51) is provided to guide the panel 10 to the last positioning roll 13.

The panel 10 passes from the last roll 13 (far right in FIGS. 1 and 2) over a pair of bottom rolls 68 and 70 which are mounted on arms 74 which in turn are mounted to pivot about the axis of the reaction roll 60 immediately adjacent thereto. A screw type actuator 72 angularly positions the arm 74 (as indicated by the arrow 73) and thereby positions the rolls 68, 70 and 17 which are mounted thereon so that these rolls are along the normal trajectory of the panel as it passes out of the tester, i.e. the arm 74 and rolls 68, 70 and 17 are similar to and positioned in the same manner as the arm 42 and rolls 40, 40 and 12 respectively at the in-feed end of the machine.

Step cams 76 (only one shown) are essentially the same as step cams 46 and operate in the same manner to adjust the relative position of the roll 17 to roll 68 as do the cams 46 to space the cooperating rolls 12 and 40 in accordance with the thickness of the panel being tested.

During the movement through the "S" shape path, forces are applied to the panel between the deflector rolls 14 and 16 and their respective reaction rolls 50 and 60 against which the panel 10 is positioned by the positioning rolls 13 that cooperate with the rolls 50 and 60. All of the other rolls merely ensure that the panel stays in its normal path or trajectory and do not exert any significant forces on the panel as this would distort the loading, i.e. in operation the "S" shaped path of travel is determined and the rolls 40 are positioned to coincide with the curvature imparted to the panel via position of the roll 14 so that there is no load applied to the panel by rolls 40. The panel then passes from the cooperating pair of rolls 50 and 13 on the other side of the roll 14 into the nip formed by the the first pair of cooperating rolls 13 and 60 which are positioned by moving of the frame 34 so that the nip between the rolls 13 and 60 is along the normal trajectory of the panel as it leaves the last set of rolls 13 and 50. This normal trajectory will match with the normal path of the panel entering the second deformation station and defined by the curvature imparted to the panel by the rolls 16 and 60. The rolls 17, 68 and 70 are positioned via the actuator 72 to align with the path of travel of panel as it passes from the last set of rolls 13 and 60 (extreme right in FIGS. 1 and 2) out of the machine.

Certain of the rolls are driven to move the panel through the machine.

FIGS. 4, 5 and 6 illustrate the first loading frame 32 in somewhat more detail.

The actuators move the step cams and stops so as to position all of the rollers in a preset position for each of the selected nominal thicknesses of panel to be tested. Position feed back sensors are provided on the actuators to ensure that all of the step cams and stops are in the correct position and all actuators are controlled by the micro-processor 22. Once the rolls are positioned in accordance with the selected nominal thickness, a panel may be passed through the testing machine which will actuate the load cells 18 to indicate the load for the particular deflection of the panel and the temperature sensor to sense the temperature. These figures are utilized with the algorithm described herewith in a microprocessor to determine the values for stiffness and strength of the panel at ambient or end use temperature.

The Modulus of Elasticity (MOE) figures for panels at ambient temperature were correlated from MOE figures of the panels determined by testing at elevated temperature using an algorithm which was produced from test results of fifty 7/16th of an inch thick panels.

$$MOE_{Ambient} = \frac{1}{A + B(\text{Temp})_{Ambient}} \quad 1$$

$$B = \frac{\frac{b}{MOE_{Elevated}} + a}{1 + ((\text{Temp})_{Elevated} - 60)b} \quad 2$$

$$A = \frac{1}{MOE_{Elevated}} - B \times (\text{Temp})_{Elevated} \quad 3$$

where
a = 0.0005879
b = 0.001125
MOE = $(10)^6$ psi = Modulus of Elasticity
Temp = °C.

Table I illustrates the results from the prediction algorithm for different nominal sample thicknesses and shows standard deviation of differences of the MOE for the listed samples.

The system repeatability is illustrated in Table II for four different thicknesses of panel.

TABLE I.

| Sample Thickness* (inches) | No. of Samples | Mean MOE at Ambient Temp Mpsi** | Mean Diff Between Calculated and Actual Mpsi** | Standard Deviation of Differences Mpsi** |
|---|---|---|---|---|
| 3/8 | 96 | 590 | 23 | 20.9 |
| 7/16 | 96 | 608 | 30 | 18.9 |
| 1/2 | 50 | 551 | 32 | 11.9 |
| 5/8 | 40 | 641 | 34 | 15.5 |
| 21/32 | 38 | 709 | 65 | 21.5 |
| 3/4 | 36 | 635 | 20 | 10.8 |

*Results are based on nominal thicknesses.
**Mpsi = one thousand pounds per square inch

TABLE II

| System Repeatability | | | |
|---|---|---|---|
| Thickness (inches) | Sample Size | MOE (Mean Mpsi) | Repeatability (95% Confidence) (Mpsi) |
| 3/8 | 30 | 802 | ±24.0 |
| 7/16 | 24 | 747 | ±17.6 |
| 5/8 | 30 | 680 | ±17.8 |
| 3/4 | 28 | 854 | ±13.5 |

The functions of the micro-processor are:
1. To set up the panel tester for specific panel thickness.
2. To perform data acquisition and determine elevated and ambient temperature end use MOEs.
3. To grade and mark panels according to predetermined MOE levels.
4. To report statistics of the results.

Figure 7:
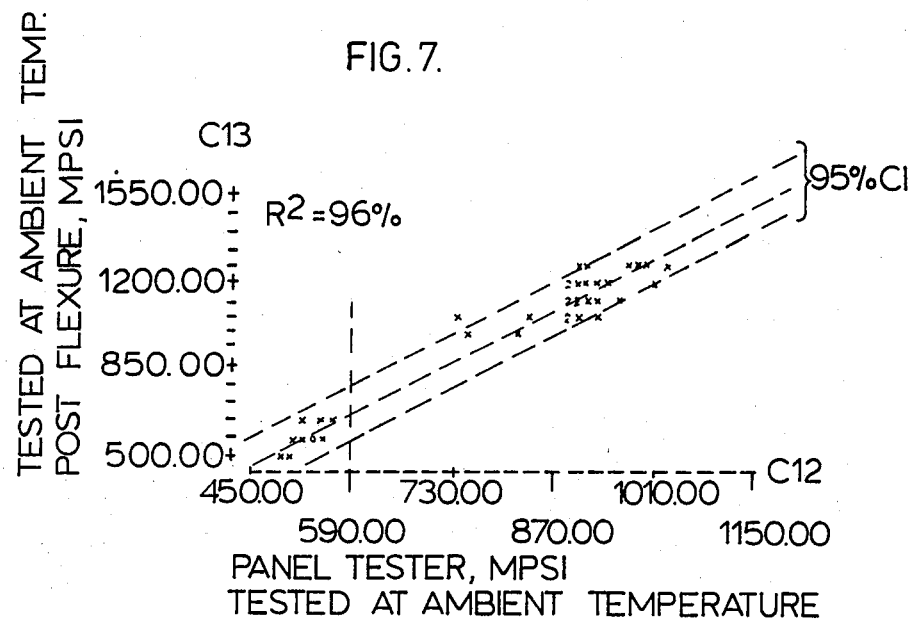
FIG. 7 is a graph showing correlation of the panel tester results with post-flexure results.
Figure 8:
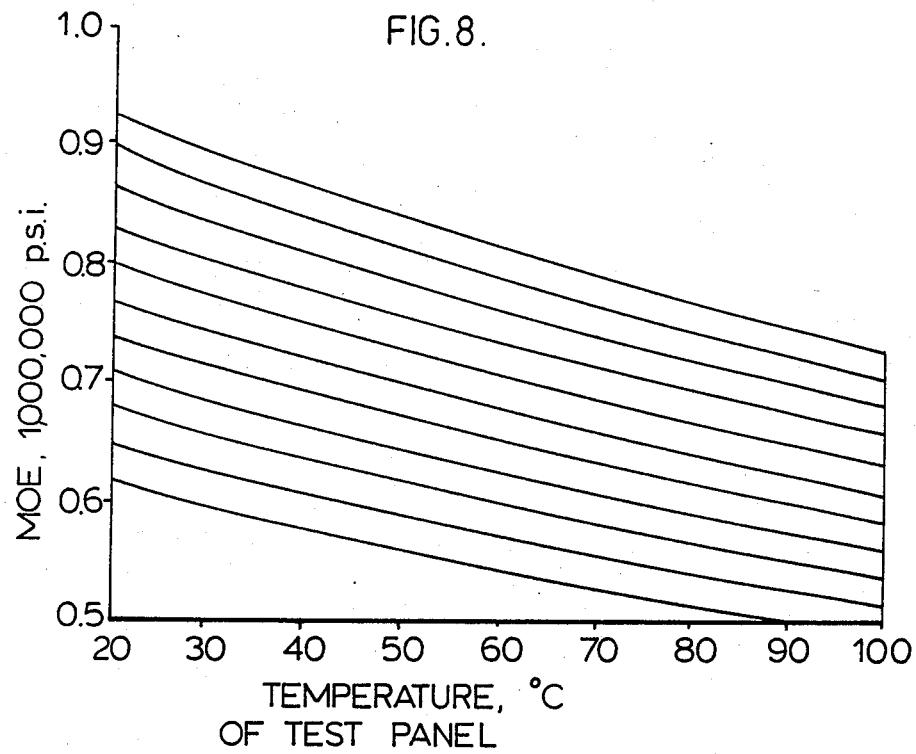
FIG. 8 shows a graph of a predicted algorithm of MOE against temperature.

FIG. 7 illustrates a correlation of panel tester results with post-flexure results when the panel is tested ambient temperature. FIG. 8 shows a graph of the MOE against temperature according to the prediction algorithm, equation 1 above.

Various changes may be made to the apparatus and process described herein without departing from the scope of the present invention which is limited only by the following claims.

We claim:
1. An apparatus for determining the stiffness at ambient temperature of a panel tested at elevated temperature while moving in a "S" shaped path comprising first deflector means between a first pair of reaction rolls relatively positioned to bend the panel in a first direction into a first curved shape of one portion of said "S" shaped path, second deflector means between a second pair of reaction rolls relatively positioned to bend said panel in a second direction opposite to said first direction into a second curved shape of another portion of said "S" shaped path, first and second load measuring means measure the loads to bend said panel into said first and second curved shapes respectively, temperature sensing means to measure said elevated temperature of said panel at which said panel is being tested and computer means to determine the stiffness of said panel at ambient temperature based on said loads measured by said load measuring means and said elevated temperature sensed by said temperature sensing means.

2. The apparatus according to claim 1 wherein the deflector means each comprise a deflector roll free to rotate on an axis supported by an arm, positioning of the deflector roll being by a step cam for the predetermined bending of the panel, and wherein each load measuring means includes a load cell.

3. The apparatus according to claim 1 including an adjustment means to vary the relative position of said reaction rolls and deflector means for a predetermined bending of the panel for different thicknesses of panels to be tested.

4. The apparatus according to claim 1 wherein the temperature sensing means comprises an infra-red detector positioned adjacent said path.

5. The apparatus according to claim 1 wherein the computer means comprises a micro-processor utilizing a program that determines stiffness and strength of the panel at ambient temperature 6. The apparatus according to claim 5 wherein the micro-processor grades each panel according to preset standards of stiffness and strength.

7. The apparatus as defined in claim 1 further comprising a thickness sensing means, means connecting said thickness sensing means to said computer means.

8. An apparatus for determining the stiffness of a panel moving along an "S" shaped path comprising a main frame, a first load frame movably mounted on said main frame and carrying a first deflector means interposed between a first pair of positioning rolls and a first height adjusting means to adjust the position of said deflector means relative to said first pair of positioning rolls, a first pair of reactional rolls mounted on said main frame each forming a nip with the adjacent one of said first pair of positioning rolls, said first deflector means cooperating with said first pair of reaction rolls to deform said panel in a first direction into a first curved shape forming a first curved portion of said "S" shaped path, a sub-main frame, means adjustably mounting said sub-main frame on said main frame, a second load frame movably mounted on said sub-main frame and carrying a second deflector means interposed between a second pair of positioning rolls, a second height adjusting means to adjust the position of said second deflector means relative to said second pair of positioning rolls, a second pair of reaction rolls mounted on said sub-main frame each forming a nip with the adjacent one of said second pair of positioning rolls, said second deflector means cooperating with said second pair of reaction rolls to deform said panel in a second direction opposite to said first direction to a second curved shape forming a second curved portion of said "S" shaped path, operating means to operate said first and second height adjustment means to relatively adjust each of said first and second deflector means and said first and second pairs of positioning rolls respectively to change the curvature of said first and second curved portions and to adjust the position of said sub-main frame in accordance with a modified "S" shaped path determined by the relative repositioning of said first and second deflector means and said first and second pairs of positioning rolls respectively, and first and second load sensing means to measure the loads applied to deform the panel into first and second curved portions respectively.

9. The apparatus according to claim 8 wherein said first and said second deflector means each comprises a deflector roll free to rotate on an axis supported by an arm, said first and second height adjustment means each comprising a step cam to adjust the position of said deflector roll and each said load sensing means includes a load cell.

10. The apparatus according to claim 8 wherein the adjustment means to vary the positions of the load frames, the sub-main frame and said first and second deflector means is actuated from a single control based on thickness of the panel to be tested.

11. An apparatus as defined in claim 8 wherein said operating means also adjusts the position f said first and second load frames relative to said main and sub-main frames respectively to accommodate different panel thicknesses.

12. An apparatus as defined in claim 11 further comprising temperature sensing means to sense the temperature of said panel when said panel is tested at elevated temperature as it moves along said path and computer means to determine stiffness of said panel at ambient temperature based on loads measured by said first and second load sensing means and said elevated temperature sensed by said temperature sensing means.

13. An apparatus as defined in claim 12 wherein said computer means incorporates a program utilizing an alogrithm to determine said stiffness at ambient temperature.

14. The apparatus according to claim 13 wherein the algorithm is according to the following formula.

$$MOE_{Ambient} = \frac{1}{A + B(\text{Temp})_{Ambient}}$$

$$B = \frac{\frac{b}{MOE_{Elevated}} + a}{1 + ((\text{Temp})_{Elevated} - 60)b}$$

$$A = \frac{1}{MOE_{Elevated}} - B \times (\text{Temp})_{Elevated}$$

where
a = 0.0005879
b = 0.001125
MOE = (10)6 psi = Modulus of Elasticity
Temp = °C.

15. The apparatus according to claim 12 wherein the computer means to determine stiffness and strength of the panel includes an automatic grading means wherein each panel is graded according to preset standards of stiffness and strength.

16. The apparatus as defined in claim 12 further comprising a thickness sensing means, means connecting said thickness sensing means to said computer means.

17. The apparatus according to claim 8 wherein the height adjustment means for the first deflector means and the second deflector means each comprises a step cam.

* * * * *